United States Patent [19]

Weilbacher et al.

[11] Patent Number: 5,360,418
[45] Date of Patent: Nov. 1, 1994

[54] CONNECTOR FOR A THORACIC CATHETER

[75] Inventors: Eugene E. Weilbacher, Ellisville; Carl A. Buck, St. Louis, both of Mo.

[73] Assignee: Sherwood Medical Company, St. Louis, Mo.

[21] Appl. No.: 914,663

[22] Filed: Jul. 15, 1992

[51] Int. Cl.⁵ .................... A61M 25/00; F16L 25/00
[52] U.S. Cl. ..................... 604/283; 64/905; 285/177
[58] Field of Search ............ 604/264, 280, 283, 905, 604/29; 285/177, 93, 240

[56] References Cited

U.S. PATENT DOCUMENTS

| | | | |
|---|---|---|---|
| 2,315,792 | 4/1943 | Hoss | 285/160 |
| 2,494,774 | 1/1950 | Messick | 285/172 |
| 2,507,535 | 5/1950 | Madsen | 285/90 |
| 3,048,428 | 8/1962 | Ransom | 285/139 |
| 3,319,628 | 5/1967 | Halligan . | |
| 3,395,705 | 8/1968 | Hamilton . | |
| 3,433,505 | 3/1969 | Weatherhead, III | 285/177 |
| 3,517,669 | 6/1970 | Buono et al. . | |
| 3,690,703 | 9/1972 | Philipps | 285/177 |
| 3,713,443 | 1/1973 | Fertik . | |
| 3,820,546 | 6/1974 | Chittenden et al. . | |
| 3,851,650 | 12/1974 | Darling . | |
| 3,915,481 | 10/1975 | Marsh, Jr. | 285/176 |
| 3,934,906 | 1/1976 | Shippey et al. | 285/371 |
| 3,945,603 | 3/1976 | Fraser | 251/148 |
| 3,965,901 | 6/1976 | Penny et al. . | |
| 3,992,405 | 11/1976 | Whittell, Jr. et al. | 285/371 |
| 4,106,509 | 8/1978 | McWhorter . | |
| 4,266,813 | 5/1981 | Oliver | 285/12 |
| 4,334,538 | 6/1982 | Juhn . | |
| 4,416,273 | 11/1983 | Grimes | 128/207.16 |
| 4,418,944 | 12/1983 | Haines et al. | 285/24 |
| 4,511,163 | 4/1985 | Harris et al. | 285/177 |
| 4,729,765 | 3/1988 | Eckles et al. | 604/54 |
| 4,774,940 | 10/1988 | Linder | 128/204.18 |
| 4,792,327 | 12/1988 | Swartz | 604/22 |
| 4,793,637 | 12/1988 | Laipply et al. | 285/39 |
| 4,953,547 | 9/1990 | Poole, Jr. | 128/203.12 |
| 5,171,227 | 12/1992 | Twardowski et al. | 604/175 |

*Primary Examiner*—John D. Yasko
*Assistant Examiner*—Adam J. Cermak
*Attorney, Agent, or Firm*—Andrew J. Beck; Montgomery W. Smth; Curtis D. Kinghorn

[57] ABSTRACT

A connector and method is disclosed for connecting a thoracic catheter to a source of suction. The connector comprises a first tube approximately equal in inner diameter to the inner diameter of the main lumen of the thoracic catheter and a second tube connected to and in fluid communication with the first tube along a common longitudinal axis. The first and second tubes form a continuous non-constricted passage through the first and second tubes. In one embodiment, a connecting tube is placed over and in binding contact with the second tube at one end and in contact with the source of suction at the other end. In another embodiment, primarily for use with catheters with a funnel tip for connecting to the source of suction, the first and second tubes have inner diameters approximately equal to the inner diameter of the main lumen of the thoracic catheter. The catheter is cut near the funnel and the first and second tubes of the connector placed in the main lumen of the catheter to produce a continuous non-constricted passage through the catheter. A method for placing this catheter and connector in a patient's thoracic cavity is disclosed.

8 Claims, 4 Drawing Sheets

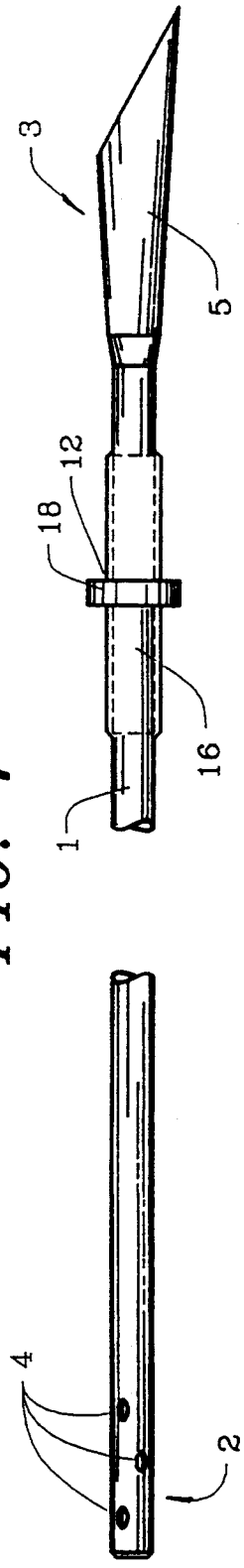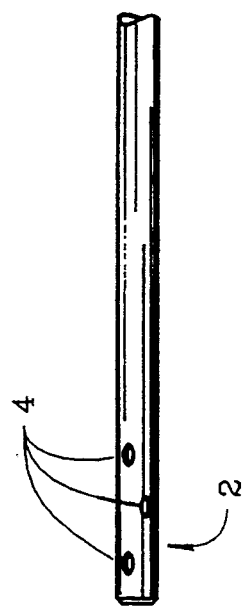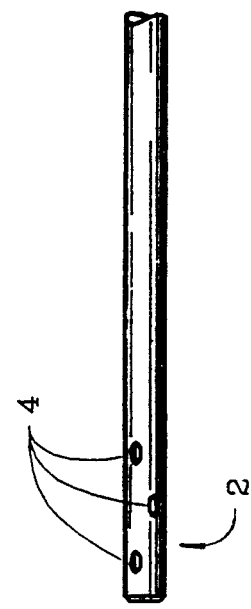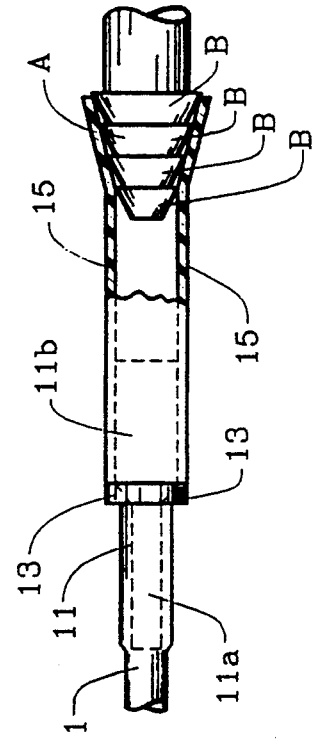
FIG. 7
FIG. 6
FIG. 4

CONNECTOR FOR A THORACIC CATHETER

BACKGROUND OF THE INVENTION

1. Field of the Invention

The instant invention relates to thoracic catheters and more specifically to a device for connecting thoracic catheters to a source of suction such as a chest drainage unit or the like.

2. Background of the Invention

Thoracic catheters are often used to remove liquids and air from the thoracic cavity as a result of surgery or injury to the thoracic cavity. A typical prior art thoracic catheter, shown in FIG. 1, is an elongated tube with a distal end 2 and a proximal end 3. The distal end 2 of the catheter is placed in the thoracic cavity and contains several openings 4 to allow the fluids in the thoracic cavity to pass into the lumen of the tube. The proximal end 3 of the catheter is connected to a source of vacuum pressure (not shown) through a CDU connector A on a device such as a chest drainage unit.

A problem with thoracic catheters, especially catheters of small diameters, has been that it is very difficult to attach the proximal end 3 of the catheter to the CDU connector A on a chest drainage unit. In the case of thoracic catheters of small diameter, this difficulty results primarily from the fact that the CDU connector A on a chest drainage unit is relatively large compared to the inside diameter of the thoracic catheter. As a result, the small diameter catheter must be stretched to fit onto the connector on the chest drainage unit. This is often a difficult procedure.

Consequently, as shown in FIG. 2, a "funnel" 5 having a larger inside diameter than the inside diameter of the proximal end 3 of thoracic catheter tube 1 is sometimes attached to the proximal end 3 of the thoracic catheter to facilitate connecting the proximal end 3 of the catheter to the CDU connector A of the chest drainage unit. However, a consequence of the funnel 5 having a larger inside diameter than the thoracic catheter is that it also has a larger outside diameter than the proximal end 3 of the catheter tube 1.

In most uses of catheters with or without "funnel" ends, the proximal end 3 of the thoracic catheter is inserted through an opening in the intercostal space between a patient's ribs from the inside of the patient's thoracic cavity to the outside. With catheters having a "funnel" end, the comparatively larger outside diameter of the funnel 5 requires a larger opening to be cut in the intercostal space than is required for catheters not having the "funnel" end. Consequently, in the case of catheters with "funnel" ends, the "funnel" which makes it easier to attach the catheter to the CDU connector of a chest drainage unit, makes it necessary to make a larger than usual cut in a patient's intercostal space in order to pass the "funnel" end through the cut.

Of course it is desirable to minimize the size of the hole cut in the intercostal wall and also to make it as easy as possible to move the catheter through the opening. Because of the size of the "funnel" end, it is desirable to make the hole in the intercostal space as small as possible and still allow the "funnel" end to pass through. The tendency to make the hole as small as possible makes it more difficult to move the catheters with the "funnel" tips through the small opening once cut.

These problems with funnel end thoracic catheters are particularly magnified in the case of pediatric patients where the size of the opening in the intercostal wall to allow the "funnel" to pass through is relatively large in comparison with the available space between the ribs in the mature adult patient.

In addition, small diameter thoracic catheters are also more likely to be used in pediatric cases. As stated above, the small diameter catheters without the "funnel" end are difficult to attach to the connector A of a chest drainage unit.

SUMMARY OF THE INVENTION

Alternate embodiments of the devices are disclosed for connecting thoracic catheters to vacuum connectors on a chest drainage unit or for allowing a thoracic catheter having a funnel tip on its proximal end to be passed through a relatively small opening in a patient's intercostal wall. The device includes a tube shaped connector having an internal diameter on at least a first end approximately equal to the internal diameter of the thoracic catheter. The first end of the connector is placed in the main lumen of a thoracic catheter.

In a thoracic catheter not having a "funnel" end, the tube shaped connector has in addition to the first end described above, a second end having an expanded internal diameter. The first end of the connector is placed in the main lumen of a thoracic catheter at the catheter's proximal end. In the preferred embodiment, the second end may be inserted into the main lumen of a flexible tube having an internal diameter approximately equal to the internal diameter of the second end. The flexible tube is then pushed onto the chest drainage unit connector. In an alternate embodiment, the second end may itself be pushed onto the relatively large CDU connector to connect the connector to the CDU connector.

In a "funnel" ended catheter, the tube of the catheter is cut distal to the funnel and inserted through the patient's intercostal space. Then, the first end of the connector is inserted into the main lumen at the proximal end of the cut portion of the catheter. The distal end of the cut portion of the catheter is placed over the exposed second end of the connector so the previously exposed second end of the connector is located within the main lumen of the cut portion of the catheter having the "funnel" end. The connector then provides a nonconstricted lumen extending through the catheter.

A method for making a thoracic catheter with a funnel tip that can be passed through a relatively small opening in a patient's intercostal wall is disclosed. In this method, the "funnel" tipped catheter is cut entirely through a distance distal to the funnel. A connector reconnects both sides of the catheter so that a continuous passage extends from the distal to the proximal end of the catheter. The distal cut portion of the thoracic catheter may be placed through a comparatively small opening cut in a patient's intercostal space. The opposed cut portion of the thoracic catheter is then reconnected to the proximal cut portion of the thoracic catheter containing the "funnel" through the use of the connector.

It is a primary object of the instant invention to provide a thoracic catheter which may be more easily connected to a source of suction such as a chest drainage unit or the like.

It is another object of the instant invention to provide a device which allows thoracic catheters of various sizes to be easily connected to vacuum connectors, including relatively large vacuum connectors.

It is an object of the instant invention to provide a thoracic catheter with a "funnel" tip which catheter can be passed through an opening in a patient's intercostal space corresponding in size to the comparatively small openings which have traditionally been used to allow a thoracic catheter to be inserted through the patient's intercostal space.

It is a further object of the instant invention to provide a connector for connecting cut opposed edges of the catheter so that a non-constricted lumen may extend from the proximal to the distal end of the catheter despite the reconnection of the cut opposed end portions.

It is also an object of the instant invention to provide a connector for reconnecting cut opposed sides of the thoracic catheter which is easy to insert and which maintains a strong connection between the cut opposed edges of the catheter.

These and other objects of the invention will be clear from the description contained herein and more specifically with reference to the following detailed description of the invention and drawings where like elements are referred to by like reference numbers.

BRIEF DESCRIPTION OF THE DRAWINGS

FIG. 4 is a side elevational view of the catheter of FIG. 1 in combination with the connector of FIG. 3 shown here inside the catheter and connecting tube in phantom.

FIG. 6 is a side elevational view of the catheter of FIG. 2 cut distal to the "funnel" to facilitate passage of the distal cut portion through an opening in a patient's intercostal space.

FIG. 7 is a side elevational view of the catheter of FIG. 6 which has been reconnected by the connector of the instant invention of FIGS. 5A,B shown here in phantom within the catheter.

DETAILED DESCRIPTION OF THE INVENTION

Figure 1:
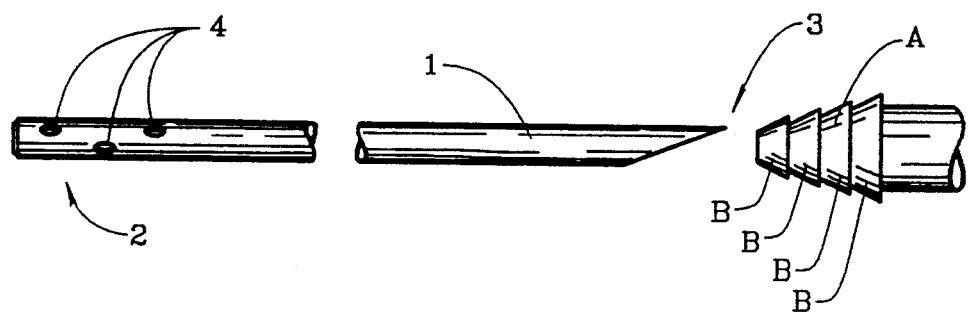
FIG. 1 is a side elevational view of a prior art thoracic catheter.
Figure 3:
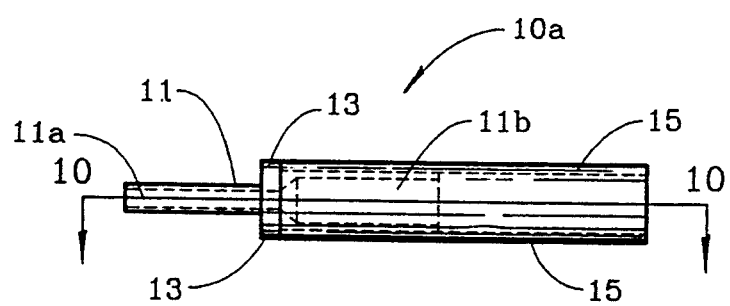
FIG. 3 is a side view of one embodiment of the connector of the instant invention.

According to the most preferred embodiment of the invention, a connector generally labelled 10a, as shown in FIG. 3, is provided which allows the catheter shown in FIG. 1 to be connected to the vacuum source A, as shown in FIG. 4. The connector 10a of FIG. 3 includes a generally tube-shaped core 11. Core 11 has an inside diameter at a small end 11a about equal to the inside diameter of tube 1 of the catheter to which the connector 10a is to be attached. An expanded end 11b of core 11 has an inside diameter significantly larger than the inside diameter of 11a. The inside diameter of expanded end 11b is about equal to the outside diameter of the CDU connector A at a point along the series of progressively larger ridges B.

Core 11 also has an integrally attached annular ring shaped stop 13 which extends around core 11 and is positioned at the transition point between the small end 11a and the expanded end 11b of core 11. The outer surface of annular stop 13 extends a small distance beyond the outer surface of the expanded end 11b of core 11.

Connector 10a also preferably includes a connecting tube 15 having an inside diameter slightly less than the outside diameter of the expanded end 11b of core 11. Connecting tube 15 is made of a tubular flexible elastomeric material and is placed over expanded end 11b so that it encases the expanded end 11b and comes in contact with the annular stop 13. In order to facilitate the placement of connecting tube 15 on the expanded end 11b, the most proximal end of the expanded end 11b may be slightly tapered moving toward the proximal end of expanded end 11b in order to allow connecting tube 15 to move more easily onto the expanded end 11b. When in position, connecting tube 15 entirely encases the expanded end 11b and is held in position by frictional contact between connecting tube 15 and the surface of expanded end 11b.

In operation, connector 10a must be attached to catheter 1. This is done by inserting small end 11a of core 11 into the main lumen of catheter 1 at the proximal end 3 of catheter 1. Small end 11a is pushed into the main lumen of catheter 1 until the end of catheter 1 comes in contact with the annular stop 13. The insertion of small end 11a through the lumen of tube 1 may be facilitated by applying a lubricous coating to the exterior surface of small end 11a as well as by manipulating small end 11a such as by grasping annular stop 13 and rotating core 11 along its longitudinal axis while applying pressure to core 11 through stop 13 in a distal direction collinear with the longitudinal axis of the main tube 1.

The expanded end 11b of core 11 must also be attached to connecting tube 15. This is done by inserting expanded end 11b into the main lumen of connecting tube 15 until connecting tube 15 comes in contact with annular stop 13. The insertion of expanded end 11b through the lumen of connecting tube 15 may also be facilitated by applying a lubricous coating to the exterior surface of expanded end 11b as well as by manipulating core 11 such as by grasping annular stop 13 and rotating core 11 around its longitudinal axis while applying pressure to core 11 through annular stop 13 in a distal direction collinear with the longitudinal axis of connecting tube 15.

As shown in FIG. 4, when a connector 10a is placed in position in catheter 1, the most proximal end of connecting tube 15 may be placed over the ridges B of CDU connector A. Because of the expanding outer diameter of the sections B, a portion of the proximal end of tube 15 will be expanded as connecting tube 15 is placed over CDU connector A. Friction and compressive forces between connecting tube 15 and the section B will hold connecting tube 15 securely in place on the ridges B of CDU connector A.

When connector 10a is connected to CDU connector A and catheter 1 as shown in FIG. 4, a continuous non-constricted passage is provided from the openings 4 through the central lumen of catheter 1 to the vacuum pressure supplied at CDU connector A.

The inside diameter of the small end 11a of core 11 should be about the same as the inside diameter of the lumen of catheter 1. Because thoracic catheters 1 come in a variety of sizes, it is intended that the small end 11a of core 11 should also come in a variety of sizes to correspond to the inside diameters of the catheters 1.

Also, the expanded end 11b of core 11 may also be produced in a variety of sizes corresponding to different sized CDU connectors A. Therefore, it is intended that connectors 10a may be made in a variety of sizes for the small end 11a and the expanded end 11b of core 11.

In addition, the length of connecting tube 15 may be varied as desired. The key feature of the length of connecting tube 15 is that when connecting tube 15 is placed over the ridges B of CDU connector A, connecting tube 15 is sufficiently long to allow CDU connector A to be moved into sealing contact between connecting tube 15 and the ridges B. In addition, tube 15 is sufficiently long for CDU connector A not to contact the proximal end of the expanded end 11b of core 11.

In a variation of this embodiment, the expanded end 11b may itself be placed in contact with CDU connector A. In this embodiment, expanded onward end 11b may need to be made of a flexible elastomeric material and be longer than is required in the previous embodiment so that expanded end 11b may be moved into contact with the ridges B of CDU connector A and so that CDU connector A may be moved a sufficient distance into expanded end 11b to achieve a sealing contact between expanded end 11b and CDU connector A.

Figure 2:
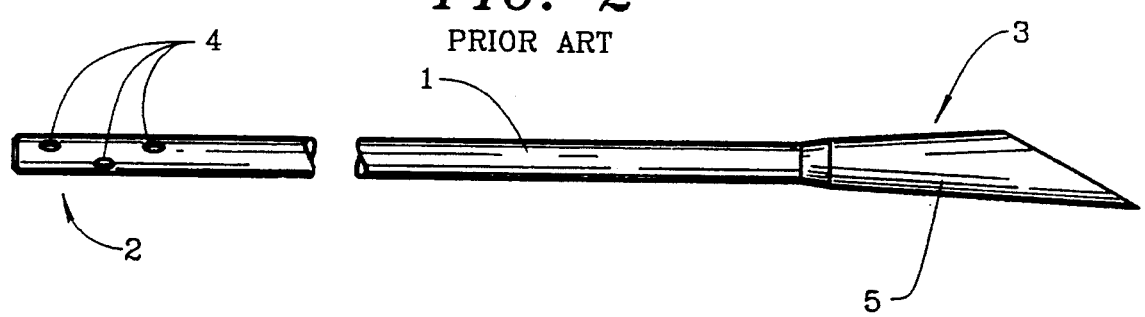
FIG. 2 is a side elevational view of a prior art thoracic catheter containing a "funnel" on the proximal end to facilitate connecting the catheter to a source of suction.

According to another embodiment of the instant invention, the thoracic catheter having a funnel 5 on its proximal end 3, shown in FIG. 2, is cut entirely through a distance distal to the funnel 5 to produce two sections as shown in FIG. 6. The cut produces a proximal cut portion 12 and a distal cut portion 14. Catheter tube 1 may be cut during the manufacturing process so that the catheter, when delivered to the doctor, has already been precut to facilitate the use of a connector 10b which will be described hereafter. Alternately, a surgeon using a "funnel" end catheter such as shown in FIG. 2, may cut the catheter tube 1 at a distance proximal to the funnel 5 at the time of the surgical procedure by means such as a scalpel or the like in order to separate the funnel 5 and a portion of the tube 1 from the main body of the tube 1.

Regardless of how the tube 1 is cut to separate the funnel 5 from the main body of the tube 1, it is a requirement of the invention that the main tube 1 be cut to allow the distal cut portion 14 of the main tube to be passed through a relatively small opening in the patient's intercostal space.

Figure 5A:
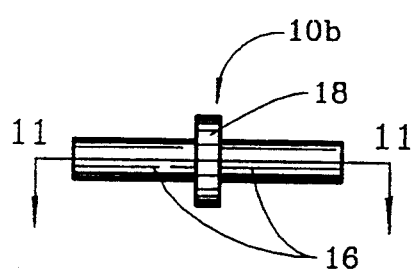
FIG. 5A is a side elevational view of an embodiment of the connector of the instant invention used with the catheter of FIG. 2.

After the surgeon has passed the distal cut portion 14 through the opening in the intercostal space, a connector 10b (FIGS. 5A, 5B) is used to connect the distal cut portion 14 with the proximal cut portion 12 of tube 1. This produces a continuous opening from the distal end 2 to the proximal end 3 of the catheter.

Figure 5B:
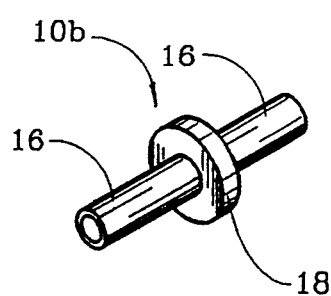
FIG. 5B is a perspective view of the connector of FIG. 5A.
Figure 8:
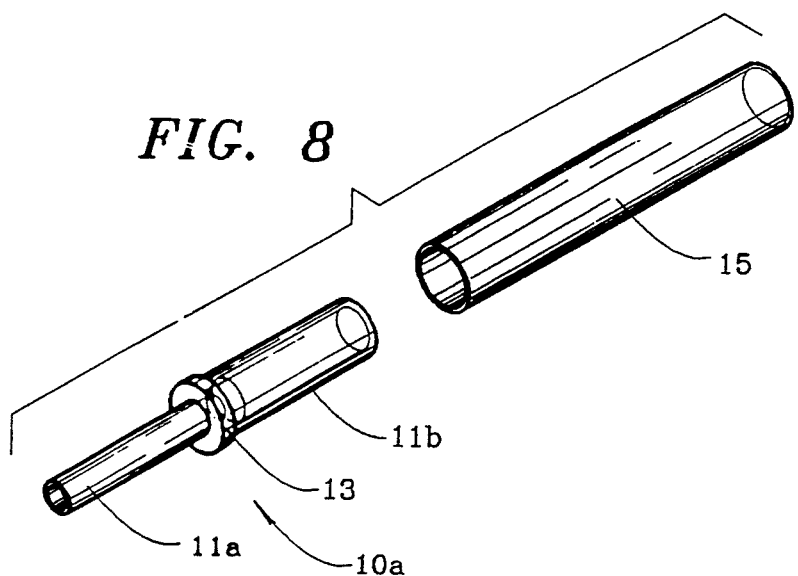
FIG. 8 is an exploded perspective view of the connector shown in FIG. 3.
Figure 9:
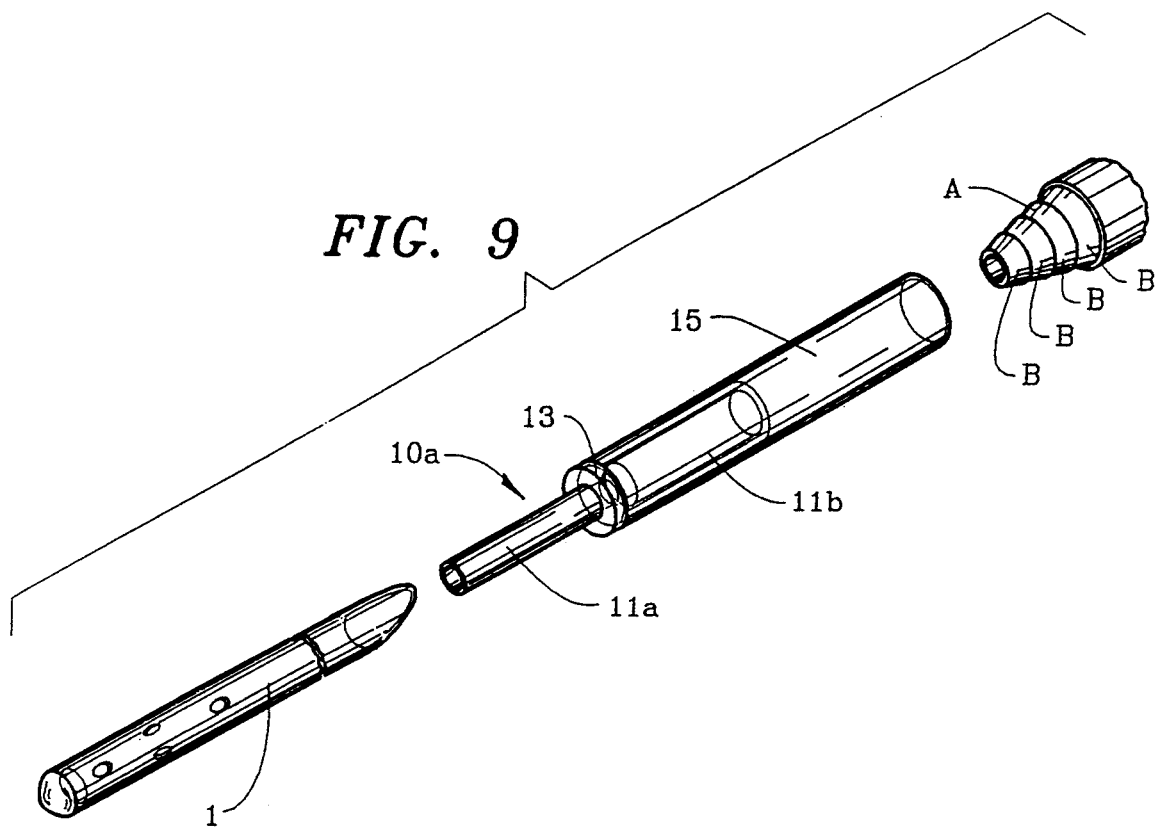
FIG. 9 is an exploded perspective view of the thoracic catheter of FIG. 1, the connector of FIGS. 3 and 8 and a CDU connector, along their common longitudinal axes.
Figure 10:
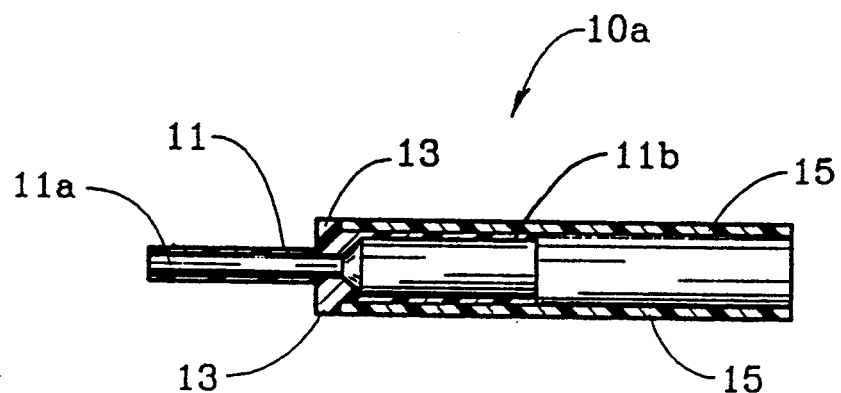
FIG. 10 is a cross sectional view of the connector shown in FIGS. 3 and 8.
Figure 11:
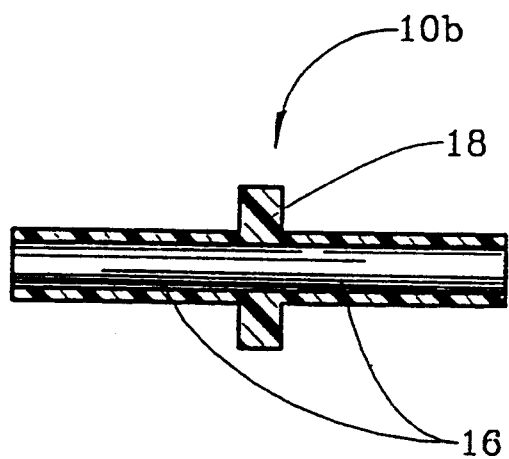
FIG. 11 is a cross sectional view of the connector shown in FIGS. 5A and 5B.

As seen in more detail in FIGS. 5B and 7, the connector 10b includes a tube 16 having an inside diameter approximately the same as the inside diameter of the main lumen of tube 1. An annular central stop 18 is located midway between the ends of connector 10b and extends away from connector 10b. Stop 18 preferably extends entirely around connector 10b.

After the surgeon has passed the distal cut portion 14 through the cut in the patient's intercostal space, the distal portion 2 of tube 1 must be reconnected to the proximal end 3 of tube 1 before the catheter can be used. To reconnect both sides of tube 1, one end of connector 10b is inserted into the main lumen of tube 1 exposed at distal cut portion 14 until distal cut portion 14 comes in contact with stop 18. The insertion of connector 10b through the lumen of tube 1 may be facilitated by applying a lubricous coating to the exterior surface of connector 10b as well as by manipulating the connector 10b such as by grasping stop 18 and rotating connector 10b around its longitudinal axis while applying pressure to connector 10b through stop 18 in a distal direction collinear with the longitudinal axis of the main tube 1.

After distal cut portion 14 has been brought into contact with stop 18, the opposite end of connector 10b is then placed in the main lumen of tube 1 exposed by proximal cut portion 12. Proximal cut portion 14 is brought in contact with stop 18. Again, the operation of moving connector 10b into the main lumen exposed by proximal cut portion 12 may be facilitated by the application of a lubricous coating to the exterior of connector 10b and by the manipulation of connector 10b relative to the tubing 1 as described above. In this regard, because connector 10b is already placed in position in the distal end of main tube 1, the proximal end of tube 1 may have to be manipulated as by rotation or the like to move the connector 10b into the lumen of the proximal end of tube 1. Of course the order of attaching the proximal and distal cut portions 12,14 of tube 1 to connector 10b described above may be reversed.

As can be seen in more detail in FIG. 7, when the connector 10b (shown in phantom within tube 1) is in position within the catheter so that both the distal cut portion 14 and the proximal cut portion 12 are in contact with stop 18, the material of the catheter is stretched around the exterior surface of connector 10b to hold connector 10b in place while still allowing material removed from the thoracic cavity through inlet openings 4 to pass unrestricted through the central opening of connector 10b.

Connectors 10a and 10b are preferably made of a material rigid enough not to collapse or kink while being put into place, as described hereafter, and while the catheter is being used. A preferred material for manufacturing the connectors 10a and 10b is a polypropylene material. In some uses, the polypropylene material should be radiation qualified for sterilization.

Although the material used in the manufacture of connectors 10a and b greatly influences its rigidity, the rigidity of the connectors 10a,b is also a function of the thickness of the material used. Therefore, the walls of core 11 and tube 16 should be of sufficient thickness to allow the connectors 10a,b not to collapse or kink but not be so thick as to render it difficult to insert into the main lumens of tube 1 and connecting tube 15 as is described herein. Regardless of the material used or its thickness, it is important that connectors a,b not collapse or kink during use so that an open channel is provided from the distal end 2 to the proximal end 3 of the catheter. Although a specific manufacturing material has been described, any material having the stated properties is within the scope of the invention.

Because catheters come in a variety of sizes typically ranging from 8 French up to 40 French, connectors 10a,b corresponding to each size catheter should ideally be provided. In these connectors 10a,b, the inside diameter of the small end 11a and of the entire connector 10b will correspond to the inside diameter of the main lumen of tube 1 so that connector 10a,b does not provide a restriction to blood and other material removed from the thoracic cavity and passing through the catheter. It has been found that the large sized connectors 10a,b corresponding to the larger size catheters are easier to insert into the main lumen of tube 1 than the small sized connectors 10a,b.

In order to differentiate the various sized connectors 10a,b, coloring may be applied to the material of the connectors 10a,b at the time of manufacture so that each size connector 10a,b would have its own color corresponding to the size catheter to which it applies. Alternately, the stops 13 and 18 may be marked with a series of indicia indicating the size catheter to which they correspond. In another alternate embodiment, one or a series of notches, indentations or the like may be cut or formed in the surface of stops 13,18 to identify the size of the particular connectors 10a,b respectively.

In understanding the instant invention in all the embodiments described herein, it may be useful to think of the connectors 10a,b as two tubes joined together along a common longitudinal axis. In the most preferred embodiment of the connector 10a, the two tubes would be the small end 11a and expanded end 11b of core 11. These two tubes have a common juncture at annular stop 13.

In the alternate embodiment of the connector 10b described herein, the two tubes are opposite ends of tube 16 which have a common juncture at annular stop 18.

The instant invention has been described in connection with a specific embodiment as well as a method for making the invention. The details of the description have been given by means of example and not for the purpose of limitation. It is clear that changes and modifications may be made to the instant invention and still be within the scope of the claims. Further, obvious changes and modifications may be made to the description contained herein.

We claim:

1. In combination, a thoracic catheter and a connector for connecting the thoracic catheter to a source of suction at a source of suction connector protruding from the source of suction, the source of suction connector having a series of annular ridges of increasing diameter, the combination comprising:
    a) a thoracic catheter having a proximal end, a distal end and a main lumen having an inner diameter and extending from the distal end to the proximal end;
    b) a first tube approximately equal in inner diameter to the inner diameter of said main lumen, said first tube having a constant outer diameter along said first tube's entire length;
    c) a second tube connected to and in fluid communication with said first tube along a common longitudinal axis, said second tube having an inner diameter larger than the inner diameter of said first tube; and,
    d) a connecting tube having an inner diameter approximately equal to the outer diameter of said second tube, said connecting tube placed over and in binding contact with said second tube, said connecting tube extending beyond the end of said second tube opposite said first tube;
    whereby said first tube is placed directly in said main lumen of said thoracic catheter and retained therein, and,
    whereby a continuous non-constricted passage is presented through said main lumen of said thoracic catheter and said first and said second tubes.

2. The combination of claim 1 wherein said connecting tube is made of a flexible elastomeric material whereby said connecting tube stretches as it is placed over said second tube.

3. The combination of claim 1 further comprising an annular stop located at the juncture of said first tube and said second tube and having a larger outer diameter than either said first or said second tube, the longitudinal axis of said annular stop aligned with the longitudinal axes of said first and said second tubes, the inner diameter of said annular stop being at least approximately equal in inner diameter to the inner diameter of the main lumen.

4. The combination of claim 3 wherein said annular stop includes means for indicating the size of said connector.

5. The combination of claim 1 wherein said second tube is made of flexible elastomeric material.

6. In combination, a thoracic catheter and a connector for connecting the thoracic catheter to a source of suction at a source of suction connector protruding from the source of suction, the source of suction catheter having a series of annular ridges of increasing diameter, the combination comprising:
    a) a thoracic catheter having a proximal end, a distal end and a main lumen having an inner diameter and extending from the distal end to the proximal end;
    b) a first tube approximately equal in inner diameter to the inner diameter of said main lumen;
    c) a second tube connected to and in fluid communication with said first tube along a common longitudinal axis, said second tube having an inner diameter larger than the inner diameter of said first tube;
    d) an annular stop located at the juncture of said first tube and said second tube and having a larger outer diameter than either said first or said second tube, the longitudinal axis of said annular stop aligned with the longitudinal axes of said first and said second tubes, the inner diameter of said annular stop being approximately equal in inner diameter to the inner diameter of said second tube, said stop for limiting the movement of the thoracic catheter over said first tube, and,
    e) a connecting tube having an inner diameter approximately equal to the outer diameter of said second tube, said connecting tube placed over and in binding contact with said second tube, said connecting tube extending beyond the end of said second tube opposite said first tube;
    whereby a continuous non-constricted passage is presented through said first and said second tubes.

7. The combination of claim 6 wherein said connecting tube is made of a flexible elastomeric material.

8. The combination of claim 6 wherein said annular stop includes means for indicating the size of said connector.

* * * * *